United States Patent [19]

Cranston

[11] 4,110,908
[45] Sep. 5, 1978

[54] ULTRASONIC DENTAL SCALER

[75] Inventor: Dale O. Cranston, Lawrence, Kans.

[73] Assignee: Litton Industrial Products, Inc., Beverly Hills, Calif.

[21] Appl. No.: 692,291

[22] Filed: Jun. 3, 1976

[51] Int. Cl.² ............................................. A61C 15/00
[52] U.S. Cl. .......................................... 32/50; 32/58; 32/DIG. 4; 310/26
[58] Field of Search .............. 32/58, 59, 50; 259/1 R, 259/DIG. 43; 310/26

[56] References Cited
U.S. PATENT DOCUMENTS

| | | | |
|---|---|---|---|
| 3,058,218 | 10/1962 | Kleesattel et al. | 32/58 |
| 3,368,280 | 2/1968 | Friedman et al. | 32/58 |
| 3,589,012 | 6/1971 | Richman | 32/58 |
| 3,930,173 | 12/1975 | Banko | 32/58 |

*Primary Examiner*—Robert Peshock
*Attorney, Agent, or Firm*—Robert A. Seldon

[57] ABSTRACT

An ultrasonic dental scaler is disclosed having a handpiece which comprises an outer shell, housing an electromechanical vibrator. The vibrator consists of a magnetostrictive transducer positioned within an energizing coil located within the shell, an acoustical impedance transformer connected at one end to the transducer, and a dental work tool connected to the other end of the transformer. The transformer provides an acoustical transmission line between the transducer and the work tool. An o-ring is mounted inside the sleeve at the balance point of the transformer to form the sole support for the vibrator. The o-ring support causes the nodal plane of the vibrator to shift from its natural position to the supported position. This forced shift of the nodal plane from its natural position causes the frequency of the system to change from its otherwise induced frequency so that the transducer length may be shortened without forfeiture of the desired operating frequency employed by such scalers.

16 Claims, 2 Drawing Figures

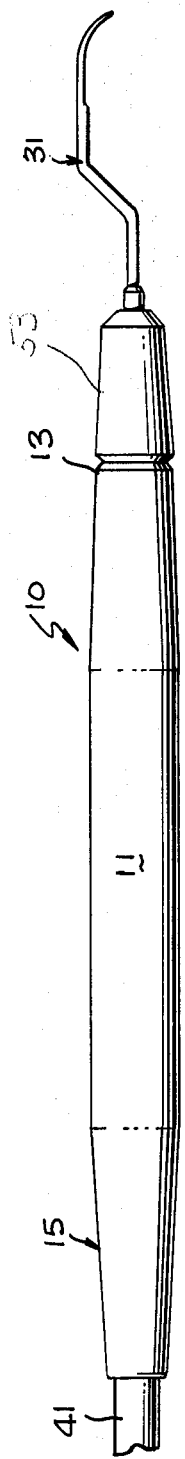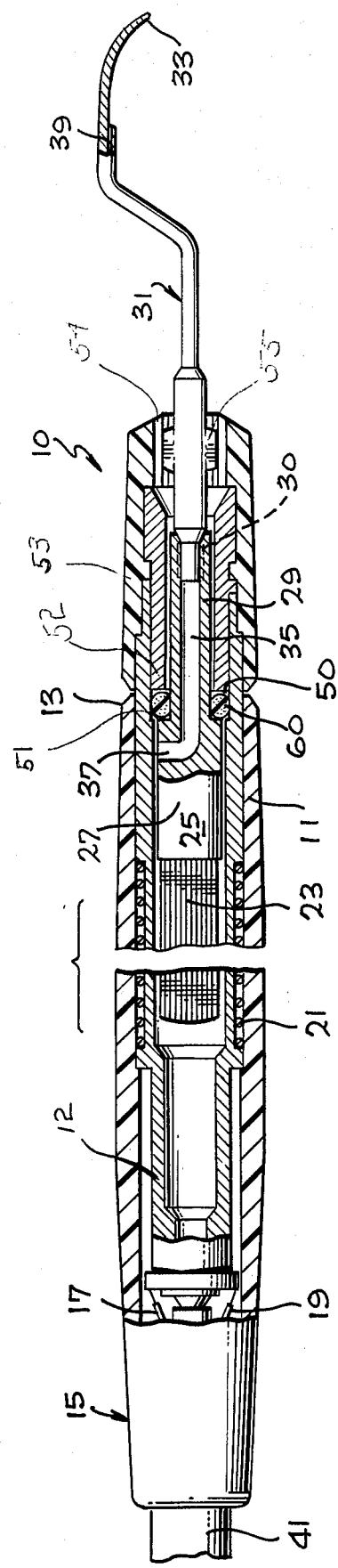

ULTRASONIC DENTAL SCALER

BACKGROUND OF THE INVENTION

1. Field of the Invention

The present invention relates generally to ultrasonic dental scalers and more particularly to the vibrating components of the scaler handpieces.

2. Description of the Prior Art

Ultrasonic dental scalers usually comprise a dental handpiece having an ultrasonic transducer positioned with an energizing coil located within a sleeve. The transducer conventionally comprises a stack of laminar plates of magnetostrictive material that is excited by the coil to longitudinally expand and contract at a frequency of approximately 20,000 cycles per second.

The transducer stack is connected at one end to an acoustical impedance transformer which in turn is connected to a dental work tool, all of which comprises the electromechanical vibrator. The transformer provides an acoustical transmission line between the transducer and the work tool. The vibrator is typically mounted in the sleeve by means of an o-ring located at a node of longitudinal vibration of the transformer when compression waves of the operating frequency are generated by the transducer. For maximum amplitude of vibration of the tool end, and for maximum transmission of working energy, the overall length of the transducer, transformer and work tool is so correlated to the frequency of the electrical oscillations delivered to the transducer, that a loop of motion of the generated compressional waves will occur at or near the working end of the tool. In other words, the overall length of the vibrator is approximately equal to an integral number of one-half wavelengths of sound waves in the particular materials comprising these components at the working frequency. The length of the transducer is also an integral number of one-half wavelengths — typically one-owing to the desire to provide the least massive system possible. It may be appreciated that size and mass are important considerations in a field in which delicate work requires instruments having an ease of handling.

In conventional dental scalers, the entire length of the vibrator is approximately 6 to 7 inches. Although it is desirable to shorten this length to make a smaller, more compact handpiece, the frequency of the system would increase to over 40,000 cycles per pound. This frequency range is considered unacceptable for dental practice.

SUMMARY OF THE INVENTION

The present invention obviates the above-mentioned shortcoming by providing a shortened handpiece that still operates at acceptable frequency ranges.

In essence, a forced nodal plane is induced in the transformer at a location other than a natural nodal plane. The location is additionally one which forces a decrease in the vibratory frequency of the vibrator assembly from its natural resonant frequency. The transducer may accordingly be shortened, with the corresponding increase in vibratory frequency; the resulting shortened vibrator assembly now produces a frequency within the acceptable range of ultrasonic scalers.

In its broadest aspect, the present invention relates to an electromechanical vibrator assembly comprising an interconnected, shortened ultrasonic transducer, an acoustical transformer, and a work tool. Means, such as an o-ring for resiliently supporting the vibrator assembly at the balance point of the transformer, are provided for inducing an unnatural node in the vibrator assembly at a position on the transformer which decreases the vibratory frequency of the transducer. It has been found that this forced shift of the nodal plane from the natural nodal plane to the balance point of the vibrator assembly causes the frequency of the system to be approximately 25,000 cycles per second.

Another advantage of the present invention is that this forced nodal shift enables a much shorter vibrator assembly to be utilized.

The features of the present invention, which are believed to be novel, are set forth with particularity in the appended claims. The present invention, both as to its organization and manner of operation, together with the further advantages thereof, may best be understood by reference to the following description taken in connection with the accompanying drawings.

BRIEF DESCRIPTION OF THE DRAWINGS

FIG. 1 is an elevational view of the dental scaler of the present invention; and FIG. 2 is a longitudinal, sectional view of a dental scaler of the present invention.

DESCRIPTION OF THE PREFERRED EMBODIMENT

Referring now to the drawings, FIGS. 1 and 2 illustrate a hand-supported dental scaler generally indicated by arrow 10, comprising an outer cylindrical casing 11 and an interior casing 12. The casing 11 has an end section 13 which is of a relatively small diameter and is open-ended. The other end section 15 of the casing 11 may be larger in diameter, and is apertured to receive a pair of conductors 17 and 19. The terminal ends of the conductors 17 and 19 are encased in suitable insulation and lead through the apertures of the end section 15 to a suitable power source. The leads of the conductors 17 and 19 are connected to an energizing coil 21 superimposed about a section of the interior casing 12.

An electromechanical vibrator assembly is located within the casing 11 and comprises a magnetostrictive transducer 23, an acoustical impedance transformer 25 and work tool 31. The magnetostrictive transducer 23 is positioned within the casing 12 at the section housing the coil 21. The transducer 23 comprises a laminated stack composed of a series of relatively thin and compactly stacked plates formed of nickel or other magnetostrictive material. One end of the transducer stack 23 is welded or soldered to an end of the tool holder 25 shaped to serve as an acoustical impedance transformer. The transformer 25 extends through the intermediate section of the outer casing 11 and comprises a main body section 27 of cylindrical construction and a tapered body section 29. The end of the tapered body section 29 contains an internally-threaded bore 30 for receiving the threaded end of the work tool 31. The work tool 31 can be of any conventional construction and usually includes an angled distal end 33. An axial bore 35 is provided within the transformer 25 and is adapted to communicate with a radial bore 37 at one end, and at the other end to an axial bore 39 formed in the work tool 31. These bores 35, 37 and 39 are provided to allow cooling fluid from the interior of the casing 11 to pass therethrough and be directed to impinge on the distal end 33 of the work tool 31 for cooling and cleansing purposes. Water is provided to the interior of the outer casing via a conduit 41 extending through an aperture of the end section 15.

An o-ring support chamber 50 is formed by a shoulder 51 on the main body section 27 of the transformer 25 and the inner end of a bushing 52 located near the open end 13 of the casing 11. The bushing 52 is force-fitted within the open end of the casing 12. The bushing 52 also functions to retain a wrench element 53 which is freely rotatable to enable its keyed aperture 54 to engage a pair of lugs 55 of the work tool 31 for detachment purposes. The o-ring support chamber 50 is preferably positioned at the balance point of the transformer. It should be noted that this balance point is different than the natural nodal plane of the combination. The chamber 50 is adapted to receive an o-ring 60 which is supported within the interior of the inner casing 12. The o-ring 60 functions not only as the sole support for the vibrator assembly, but it also functions as a seal to prevent water from within the casing 12 to leak out the open end of the end thereof. Secondary seals can also be utilized to function as auxiliary water seals.

In the preferred embodiment, the length of the transducer stack 23 is 2.620 inches, while the length of the transformer 25 is 0.975 inches. Although the length of the various work tools can vary, the illustrated work tool 31 is 1.232 inches. The o-ring support plane 50 is formed 0.400 inches from the forward end of the transformer 25 facing the work tip 31 and 0.565 inches from the opposite end facing the transducer 23.

The overall length of the vibrator 4.827 inches, which is much shorter than previous vibrators utilizing the same materials and vibrating at the same frequencies. This forced shift of the node enables the vibrator of the present invention to vibrate at the acceptable ranges for dental scalers.

It should be noted that various modifications can be made to the assembly while still remaining within the purview of the following claims.

What is claimed is:

1. A handpiece for ultrasonic scaler comprising:
a shell forming an outer casing for the handpiece;
an electromechanical vibrator comprising an acoustical impedance transformer, an ultrasonic transducer and a dental work tool, said transducer being interconnected at at least one of its ends to said transformer and said work tool, said work tool extending out of one end of said shell; and
means for supporting said vibrator at the plane located at the balance point of said transformer.

2. The combination of claim 1 wherein said support means comprises an o-ring mounted within said shell and extending around said transformer at said balance plane.

3. The combination of claim 2 wherein said ultrasonic transducer comprises a laminated stack of a series of relatively thin and compactly stacked plates formed of a magnetostrictive material.

4. The combination of claim 3 wherein said transducer stack is bonded to the one end of said transformer.

5. The combination of claim 2 wherein the length of said laminated stack is 2.620 inches.

6. The combination of claim 2 wherein said acoustical impedance transformer further includes a shoulder for retaining said o-ring at the desired location.

7. The combination of claim 2 wherein the length of said acoustical impedance transformer is 0.975 inches.

8. The combination of claim 7 wherein said plane located at the balance point of said vibrator is located 0.400 inches from the forward end of said transformer connected to said work tool.

9. The combination of claim 2 wherein the length of said work tool is 1.232 inches.

10. An ultrasonic scaler of the type normally including an outer shell,
an electrochemical vibrator assembly for producing vibrations of a frequency within an acceptable range for dental scalers including accoustical impedance transformer means, ultrasonic means and a dental work tool, and
means for supporting the vibrator within the shell, said work tool extending out from one end of the shell;
wherein the improvement comprises:
transducer means having a length of less than one-half wavelength of the vibrating frequency, and
means for inducing a non-natural nodal plane at a position along the transformer, the position being such that the transducer vibrates within the acceptable frequency range.

11. The scaler of claim 10 wherein the inducing means includes means for solely and resiliently supporting the vibrator assembly at said position and within the shell.

12. The scaler of claim 11 wherein the supporting means includes O-ring means.

13. A method for producing a compact ultrasonic dental scaler comprising the step of inducing a nodal plane at a position along the accoustic transformer member which is not at a natural nodal plane and which lowers the vibrating frequency from the natural frequency of the vibrator assembly; and
sizing the transducer to vibrate the vibrator assembly at a suitable frequency.

14. The method of claim 13 including the step of supporting the vibrator assembly solely at the induced nodal plane.

15. The method of claim 14 including the step of supporting the assembly at the balance plane of the transformer.

16. The method of claim 15 including the step of supporting the assembly by means of an O-ring.

* * * * *